United States Patent [19]
Lee et al.

[11] Patent Number: 5,989,900
[45] Date of Patent: Nov. 23, 1999

[54] PROCESS FOR PREPARING OPTICALLY ACTIVE ALLYLIC ALCOHOL DERIVATIVES

[75] Inventors: Adam Shih-Yuan Lee; Hsiu-Chih Yeh; Ohm-Guo Pan; Shyh-Fong Chen; Hao Ku, all of Taipei, Taiwan

[73] Assignee: Development Center of Biotechnology, Taiwan

[21] Appl. No.: 09/136,722

[22] Filed: Aug. 19, 1998

[51] Int. Cl.⁶ .......................... C12P 41/00; C12P 11/00; C12P 13/00
[52] U.S. Cl. .................. 435/280; 435/128; 435/130; 435/131; 435/195; 435/198
[58] Field of Search .................. 435/198, 195, 435/128, 130, 131, 280

[56] References Cited

U.S. PATENT DOCUMENTS 5,106,750  4/1992  Wong et al. .......................... 435/280

OTHER PUBLICATIONS

Caddick, S.;Jenkins, K. Chem. Soc. Rev. 1996, 447–456.
Noyori R.; Tokunaga, M.; Kitamura M. Bull. Chem. Soc. Jpn. 1995, 68, 36–55.
Ward, R.S. Tetrahedron: Asymmetry 1995, 6, 1475–1490.
Burgess, K.; Jennings, L.D. J. Am. Chem. Soc. 1991, 113, 6129–6139.
Mitsuda, S.; Nabeshima, S. Recl. Trav. Chim. Pays–Bas 1991, 110, 151–154.
Burgess, K.; Jennings, L.D.. J. Am. Chem. Soc. 1990, 112, 7434–7436.
Panek, J.S.; Clark, T.D. J. Org. Chem. 1992, 57, 4323–4326.
Noyori, R.; Suzuki, M. Angew. Chem. Int. Ed. Engl. 1984, 23, 847–876.
Caton, M.P.L. Tetrahedron 1979, 35, 2705–2742.
Taylor, R.J.K. Synthesis 1985, 364–392.
Samuelsson, B., Angew. Chem. Int. Ed. Engl. 1983, 22, 805–815.
Vane, J.R. Angew. Chem. Int. Ed. Engl. 1983, 22, 741–752.
Bergstorm, S. Angew. Chem. Int. Ed. Engl. 1983, 22, 858–866.
Nelson, N.A.; Kelly, R.C.; Johnson, R.A. Chem. Eng. News 1982 33(60), 30–44.
Roberts, S.M.; Scheinmann, F. New Synthetic Routes to Prostaglandins and Thromboxanes, Academic Press: New York 1982.
Newton, R.F.; Roberts, S.M. Tetrahedron 1980, 36, 2163–2196.
Nicolaou, K.C.; Gasic, G.P.; Barnette, W.E. Angew. Chem. Int. Ed. Engl. 1978, 17, 293–312.
Mitra, A. Synthesis of Prostaglandins, Wiley–Interscience: New York, 1977.
Gooding, O.W.; Beard, C.C.; Cooper, G.F.; Jackson, D.Y. J. Org. Chem. 1993, 58, 3681–3686.
Gooding, O.W. J. Org. Chem. 1990, 55, 4209–4211.
Suzuki, M.; Yanagisawa, A.; Noyori, R.J. Am. Chem. Soc. 1988, 110, 4718–4726.
Suzuki, M.; Yanagisawa, A.; Noyori, R.J. Am. Chem. Soc. 1985, 107,. 3348–3349.
Morita, Y.; Suzuki, M.; Noyori R. J. Org. Chem. 1989, 54, 1785–1878.
Pirkle, W.H. Asymmetric Synthesis, Morrison J.D. ed., Academic Press: New York, 1983, vol. 1, pp. 125–152; and Williams, A.; Ibrahim, I.T. Chem. Rev. 1981, 81, 589–636.

*Primary Examiner*—Herbert J. Lilling
*Attorney, Agent, or Firm*—Scully, Scott, Murphy & Presser

[57] ABSTRACT

A process for preparing optically active allylic alcohol derivatives comprises reacting a racemic mixture of the following formula I

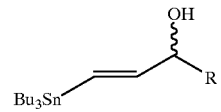

wherein R is alkyl, alkenyl, or substituted or unsubstituted aryl or arylalkyl;
with acetate or anhydride under the catalysis of Pseudomonase AK, PS or K-10 lipase in the presence of an organic solvent.

13 Claims, No Drawings

PROCESS FOR PREPARING OPTICALLY ACTIVE ALLYLIC ALCOHOL DERIVATIVES

FIELD OF THE INVENTION

The present invention relates to an enzymatic resolution process for preparing optically active allylic alcohol derivatives. The derivatives can be further transformed into a silylated compound to synthesize prostaglandins and their derivatives.

BACKGROUND OF THE INVENTION

The prostaglandins (PGs), a group of natural products occurring in animal tissues, have attracted widespread attention over the past thirty years because of their diverse pharmacological properties and potential clinical applications in a number of therapeutic areas. Samuelsson, B. *Angew. Chem. Int. Ed. Engl.* 1983, 22, 805; Vane, J. R. *Angew. Chem. Int. Ed. Engl.* 1983, 22, 741; Bergstorm, S. *Angew. Chem. Int. Ed. Engl.* 1993, 22, 858 and Nelson, N. A.; Kelly, R. C.; Jhonson, R. A. *Chem. Eng. News* 1982, 33(60), 30 are referrend to herein for reference. Since the elucidation of their structures in the early 1960s, tremendous efforts have been made for the realization of an efficient chemical synthesis. This is because a sufficient supply of such is very rare, and naturally occurring local hormones rely solely on their total synthesis. Roberts, S. M.; Scheinmann, F. *New Synthetic Routes to Prostaglandins and Thromboxanes*, Academic Press: New York, 1982; Newton, R. F.; Roberts, S. M. *Tetrahedron* 1980, 36, 2163; Nicolaou, K. C.; Gasic, G. P.; Barnette, W. E. *Angew. Chem. Int. Ed. Engl.* 1978, 17, 293; Bindra, J. S.; Bindra, R. *Prostaglandin Synthesis*, Academic Press: New York, 1977 and Mitra, A. *Synthesis of prostaglandins*, Wiley-Interscience: New York, 1977 are referred to herein for reference.

For the time being, the potentially most direct and flexible route to prostaglandins is the three component coupling approach. The approach relates to reacting optically active 4-oxygenated 2-cyclopentenone derivatives 3 with organocopper reagents having ω-chain (RωCu) to obtain the enolate 4. Then, the PGs are obtained by the alkylation of the enolate 4 with alkyl halides having α-chain (Rα-X) (see Scheme 1, Path A). The references concerning the three component coupling approach include Gooding, O. W.; Beard, C. C.; Cooper, G. F.; Jackson, D. Y. *J. Org. Chem.* 1993, 58, 3681–3686; Gooding, O. W. *J. Org. Chem.* 1990, 55, 4209–4211 and Suzuki, M.; Yanagisawa, A.; Noyori, R. *J. Am. Chem. Soc.* 1988, 110, 4718–4726. Exploitation of this three component coupling methodology has, however, been impeded by the inability to directly alkylate the enolate 4 with the alkyl halides having α-chain (Rα-X). Thus, the desired product, prostaglandins cannot be obtained because of the by-reaction (see Scheme 1, Path B).

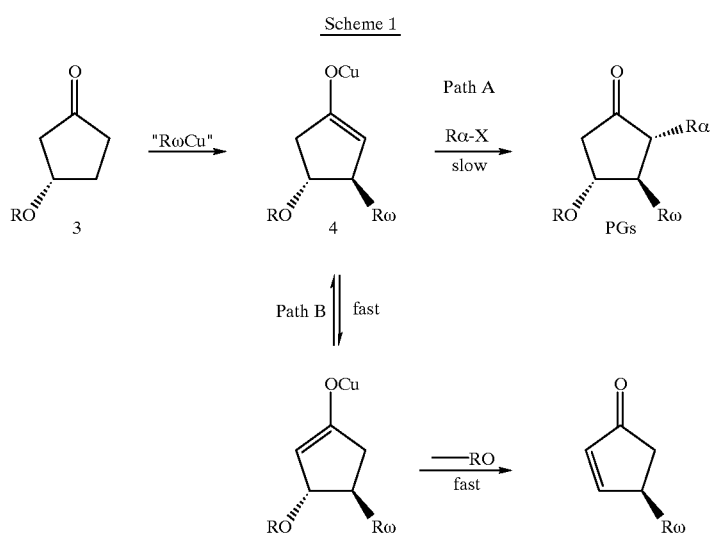

Scheme 1

Suzuki, M.; Yanagisawa, A.; Noyori, R. *J. Am. Chem. Soc.* 1985, 107, 3348 and Morita, Y.; Suzuki, M.; Noyori, R. *J. Org. Chem.* 1989, 54, 1785 have successfully overcome the abovementioned problem by employing copper to tin transmetallation at the enolate 4 stage affording a less basic stannyl enolate which retained its reactivity toward α-chain alkyl iodide (Rα-X).

Accordingly, it is a prerequiste for further synthetic application of prostaglandins to further silylate the prepared optically active allylic alcohol derivatives to the compound 5 and provide a direct and effective organocopper reagents having ω-chain (RωCu) (see Scheme 2). Noyori, R.; Suzuki, M. *Angew. Chem. Int. Ed. Engl.* 1984, 23, 847–876; Caton, M. P. L. *Tetrahedron* 1979, 35, 2705–2742 and Taylor, R. J. K. *Synthesis* 1985, 364–392 are referred to herein for reference.

Scheme 2

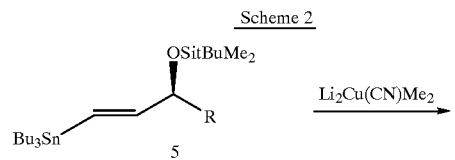

-continued

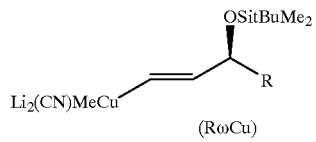

SUMMARY OF THE INVENTION

It is an object of the present invention to provide a process for preparing optically active allylic alcohol derivatives, which relates to the use of an enzymatic resolution for the separation of sinister (S-) enantiomer.

DETAILED DESCRIPTION OF THE INVENTION

The present invention relates to an enzymatic resolution process, which separates the racemic mixture of the following formula I

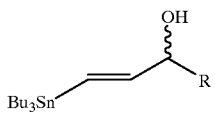

wherein R is alkyl, alkenyl, or substituted or unsubstituted aryl or arylalkyl;

into sinister (S-) and rectus (R-) enantiomers with an enzyme. The sinister (S-) enantiomer is an optically active allylic alcohol derivative which is a potential ω side chain compound of prostaglandins and can be further silylated to the compound for the synthesis of prostaglandins and their derivatives.

The method of using an enzymatic method for the separation of a racemic mixture into sinister (S-) and rectus (R-) enantiomers is disclosed in Caddick, S.; Jenkins, K. *Chem. Soc. Rev.* 1996, 447–456; Noyori, R.; Tokunaga, M.; Kitamura, M. *Bull. Chem. Soc. Jpn.* 1995, 68, 36–56 and Ward, R. S. *Tetrahedron: Asymmetry* 1995, 6, 1475–1490. The method of using Pseudomonase AK lipase for the separation of unsaturated alcohols is disclosed in Burgess, K.; Jennings, L. D. *J Am. Chem. Soc.* 1991, 113, 6129–6139; Mitsuda, S.; Nabeshima, S. *Rec. Trav. Chim. Pays-Bas* 1991, 110, 151–154; Burgess, K.; Jennings, L. D. *J. Am. Chem. Soc.* 1990, 112, 7434–7436 and Panek, J. S.; Clark, T. D. *J. Org. Chem.* 1992, 57, 4323–4326.

The present invention unexpectedly found that Pseudomonase AK, PS or K-10 lipase can catalyze the enantioselective transesterification of a racemic mixture of the following formula I

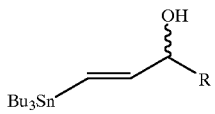

wherein R is alkyl, alkenyl, or substituted or unsubstituted aryl or arylalkyl;
with acetate or anhydride in an organic solvent. It is noted that the group of Bu₃Sn present in the racemic mixture of the formula I can control the orientation of the enantioselective transesterification to ensure that the esterification occurs in the rectus (R-) enantiomer. Accordingly, the process of the invention can separate the racemic mixture of the formula I into the sinister (S-) enantiomer 1 and the corresponding acetate of rectus (R-) enantiomer 2 which are as follows:

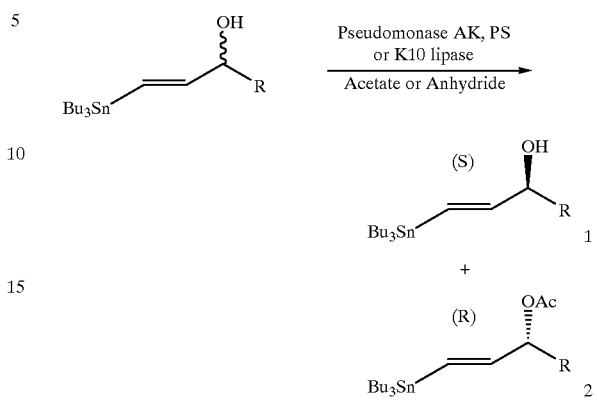

In the invention, the substituent R of the racemic mixture of the formula I is alkyl, alkenyl, or substituted or unsubstituted aryl or arylalkyl, wherein the preferred alkyl is $C_1$–$C_{10}$ alkyl, the preferred alkenyl is $C_1$–$C_8$ alkenyl, the preferred aryl is phenyl, the preferred arylalkyl is phenylalkyl (wherein the preferred alkyl is $C_1$–$C_{10}$ alkyl), the aryl or arylalkyl is substituted by alkyl, alkoxy, alkylthio or cyano.

The acetate used in the invention may be alkyl acetate and alkenyl acetate, wherein the preferred alkyl acetate is methyl acetate and ethyl acetate, and the preferred alkenyl acetate is vinyl acetate. The most preferred acetate is vinyl acetate.

The anhydride used in the invention may be formic anhydride, acetic anhydride or propionic anhydride.

The organic solvent used in the invention may be selected from the group consisting of methyl ether, ethyl ether, benzene, toluene, xylene, hexane, chloroform, dioxane, tetrahydrofuran, cyclohexane, N,N-dimethylformamide, cyanomethane, isopropyl ether, butyl ether, dichloromethane, and tert-butyl methyl ether. The preferred organic solvent is selected from the group consisting of ethyl ether, toluene, hexane, and chloroform. The more preferred organic solvent is hexane.

The reaction product and esterified enantiomer obtained from the present invention can be separated by any conventional separation method. The preferred method is column separation. The column separation method comprises passing the concentrated reaction product through a column packed with silica gel ($SO_2$) and then eluting with ethyl acetate and hexane to separate the product into sinister (S-) enantiomer and esterified rectus (R-) enantiomer.

The following examples are offered for illustrating the workability of the invention but not intended to limit the scope of the invention in any respect and should not be so construed.

EXAMPLES

Examples 1–12

(A) Enzymatic resolution for preparing optically active allylic alcohol derivatives A solution of 1.0 equivalent of a racemic mixture (as shown in Table 1, totally 12 compounds numbered 1–12), the enzyme Pseudomonas AK (Amano Company, Japan; ½ mass equivalent of the racemic mixture), 4.0 equivalents of vinyl acetate and molecular sieves (4A) in hexane (0.1 M) is stirred for 1.3–280 hours. The enzyme is filtered with filter paper and the filtrate is washed once with brine, dried with MgSO$_4$, filtered, and then hexane is removed under reduced pressure. The separation of the sinister (S-) enantiomer and the esterified rectus (R-) enantiomer are achieved on a chromatograph (with silica gel and vinyl acetate/hexane). The yield and $[\alpha]_D$ are shown in Table 1.

(B) Determination of enantiomeric excess (ee %)

The enantiomeric excess of sinister (S-) enantiomer is determined by $^{19}$F-NMR spectral analysis of its Mosher's ester derivative 6 (see Scheme 3).

Scheme 3

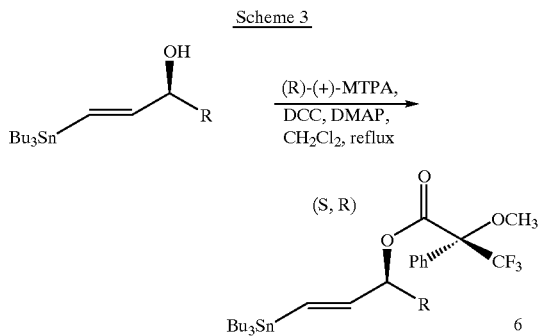

A solution of 1.0 equivalent of sinister (S-) enantiomer, 2.0 equivalent of 1,3-dicyclohexylcarbodiimide (DCC), 1.0 equivalent of 4-dimethylaminopyridine (DMAP) and 1.5 equivalent of αmethoxy-α-(trifluoromethyl)phenylacetic acid ((R)-(+)-MPTA) in CH$_2$Cl$_2$ is refluxed for 5 hours and then more 0.5 equivalent of α-methoxy-α-(R)-(+)-MPTA is added. After refluxing for 5 hours, the reaction mixture is cooled to room temperature and passed through a 3 cm Celite column. The eluate is concentrated and passed through a 3 cm silica gel column (5% ethyl acetate/hexane) and then the solvent is removed under reduced pressure. Further purification is achieved on a chromatograph with silica gel and 5% ethyl acetate/hexane. The $^{19}$F-NMR spectra are recorded at 470.5 MHz with CDCl$_3$ as solvent and trifluorotoluene as external standard. The enantiomeric excess (ee %) is determined by measuring the Mosher's ester derivative of the sinister (S-) enantiomer. The results are table 1.

TABLE 1

| No. | Racemic mixture R substituent | Enzymatic resolution Stirring time | sinister (S-) enantiomer yield % (ee %) | $[\alpha]_D$ | esterified rectus (R-) enantiomers yield % (ee %) | $[\alpha]_D$ |
|---|---|---|---|---|---|---|
| 1 | nC$_5$H$_{11}$— | 3 | 45 (>99) | +6.77 (c 0.39, CH$_3$OH) | 44 (86) | +44.75 (c 0.17, CH$_2$Cl$_2$) |
| 2 | CH$_3$— | 2 | 47 (>99) | −1.45 (c 0.27, CH$_3$OH) | 47 (>99) | +56.81 (c 0.33, CH$_2$Cl$_2$) |
| 3 | iPr— | 119 | 47 (>93) | +2.06 (c 0.16, CHCl$_3$) | 45 (85) | +35.99 (c 0.35, CHCl$_3$) |
| 4 | iBu— | 119 | 41 (>98) | −4.57 (c 0.26, CHCl$_3$) | 49 (96) | +51.15 (c 0.56, CHCl$_3$) |
| 5 | CH$_2$=CH—CH$_2$— | 1.3 | 48 (>99) | +4.03 (c 0.49, CHCl$_3$) | 48 (80) | +32.49 (c 0.57, CHCl$_3$) |
| 6 | C$_4$H$_9$–C(=CH$_2$)–CH$_2$– | 280 | 47 | +15.12 (c 0.073, CHCl$_3$) | 48 | +40.219 (c 0.106, CHCl$_3$) |
| 7 | Ph— | 20 | 47 (86) | −2.92 (c 0.33, CH$_3$OH) | 48 (96) | +12.84 (c 0.37, CH$_2$Cl$_3$) |
| 8 | p-MeO—Ph— | 68 | 42 | −3.77 (c 0.33, CHCl$_3$) | 40 | −7.33 (c 0.27, CHCl$_3$) |
| 9 | p-MeS—Ph— | 68 | 44 | — | 40 | −2.99 (c 0.22, CHCl$_3$) |
| 10 | PhCH$_2$— | 87 | 43 (93) | +6.05 (c 0.28, CHCl$_3$) | 43 (93) | +23.03 (c 0.39, CHCl$_3$) |

TABLE 1-continued

| No. | Racemic mixture R substituent | Enzymatic resolution Stirring time | sinister (S-) enantiomer | | esterified rectus (R-) enantiomers | |
|---|---|---|---|---|---|---|
| | | | yield % (ee %) | $[\alpha]_D$ | yield % (ee %) | $[\alpha]_D$ |
| 11 | p-CN-ph- | 72 | 38 | −24.61 (c 0.031, CHCl$_3$) | — | — |
| 12 | p-F-ph- | 48 | 41 | −6.25 (c 0.028, CHCl$_3$) | 45 | +12.05 (c 0.059, CHCl$_3$) |

We claim:

1. A process for preparing optically active allylic alcohol derivatives comprises reacting a racemic mixture of the following formula I

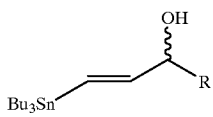

wherein R is alkyl, alkenyl, or substituted or unsubstituted aryl or arylalkyl;

with acetate or anhydride under the catalysis of Pseudomonase AK, PS or K-10 lipase in the presence of an organic solvent.

2. The process according to claim 1, wherein the alkyl is $C_1$–$C_{10}$ alkyl.

3. The process according to claim 1, wherein the akenyl is $C_1$–$C_8$ alkenyl.

4. The process according to claim 1, wherein the aryl is phenyl and the arylalkyl is phenylalkyl.

5. The process according to claim 1, wherein the aryl or arylalkyl is substituted by alkyl, alkoxy, alkylthio, or cyano.

6. The process according to claim 1, wherein the acetate is alkyl acetate and alkenyl acetate.

7. The process according to claim 6, wherein the alkyl acetate is methyl acetate or ethyl acetate.

8. The process according to claim 6, wherein the alkenyl acetate is vinyl acetate.

9. The process according to claim 1, wherein the anhydride is formic anhydride, acetic anhydride or propionic anhydride.

10. The process according to claim 1, wherein the organic solvent is selected from the group consisting of methyl ether, ethyl ether, benzene, toluene, xylene, hexane, chloroform, dioxane, tetrahydrofuran, cyclohexane, N,N-dimethylformamide, cyanomethane, isopropyl ether, butyl ether, dichloromethane and tert-butyl methyl ether.

11. The process according to claim 10, wherein the organic solvent is selected from the group consisting of methyl ether, ethyl ether, benzene, toluene, xylene, hexane and chloroform.

12. The process according to claim 11, wherein the organic solvent is selected from the group consisting of ethyl ether, toluene, hexane and chloroform.

13. The process according to claim 12, wherein the organic solvent is hexane.

* * * * *